(12) United States Patent
Hojo et al.

(10) Patent No.: US 8,828,374 B2
(45) Date of Patent: *Sep. 9, 2014

(54) SUSTAINED PHEROMONE RELEASER

(75) Inventors: Tatsuya Hojo, Joetsu (JP); Ryuichi Saguchi, Joetsu (JP); Takehiko Fukumoto, Joetsu (JP); Noboru Aiba, Joetsu (JP)

(73) Assignee: Shin-Etsu Chemical Co., Ltd. (JP)

( * ) Notice: Subject to any disclaimer, the term of this patent is extended or adjusted under 35 U.S.C. 154(b) by 1409 days.

This patent is subject to a terminal disclaimer.

(21) Appl. No.: 11/257,957

(22) Filed: Oct. 25, 2005

(65) Prior Publication Data

US 2006/0093638 A1  May 4, 2006

(30) Foreign Application Priority Data

Oct. 29, 2004 (JP) ................. 2004-315176

(51) Int. Cl.
- *A01N 25/00* (2006.01)
- *A01N 25/08* (2006.01)
- *A01N 25/34* (2006.01)
- *A01N 25/18* (2006.01)

(52) U.S. Cl.
CPC ..................... *A01N 25/18* (2013.01)
USPC .............. 424/84; 424/405; 424/409; 424/412

(58) Field of Classification Search
USPC ................... 424/405, 84, 409, 412
See application file for complete search history.

(56) References Cited

U.S. PATENT DOCUMENTS

| | | | |
|---|---|---|---|
| 4,017,030 A | 4/1977 | Coplan et al. | |
| 4,600,146 A | 7/1986 | Ohno | |
| 4,715,536 A * | 12/1987 | Capizzi et al. | 239/54 |
| 4,734,241 A * | 3/1988 | Yamamoto et al. | 424/408 |
| 4,834,745 A * | 5/1989 | Ogawa et al. | 604/890.1 |
| 4,923,119 A * | 5/1990 | Yamamoto et al. | 239/55 |
| 5,002,971 A | 3/1991 | Becker et al. | |
| 5,278,141 A | 1/1994 | Berliner | |
| 6,065,687 A * | 5/2000 | Suzuki et al. | 239/44 |
| 6,355,236 B2 * | 3/2002 | Ishino et al. | 424/84 |
| 6,419,943 B1 | 7/2002 | Sakurada et al. | |
| 6,806,293 B1 * | 10/2004 | Zamir | 514/738 |
| 2005/0235400 A1 | 10/2005 | Campbell et al. | |
| 2008/0187597 A1 * | 8/2008 | Saguchi et al. | 424/520 |

FOREIGN PATENT DOCUMENTS

| | | |
|---|---|---|
| DE | 2641630 A1 | 8/1977 |
| EP | 0243007 A2 | 10/1987 |
| EP | 0342126 A2 | 11/1989 |
| EP | 0540932 | 5/1993 |
| EP | 0540932 A1 | 5/1993 |
| EP | 0913088 A1 | 5/1999 |
| EP | 0938842 A1 | 9/1999 |
| EP | 0938842 A1 | 9/1999 |
| JP | 62-198201 | 9/1987 |
| JP | 02-069902 | 3/1990 |
| JP | 11-069936 | 3/1999 |
| JP | 11-279011 | 10/1999 |
| JP | 2004-277310 | 10/2004 |
| WO | WO 88/03755 A1 | 6/1988 |

OTHER PUBLICATIONS

Methyl Myristate, Sigma Aldrich, online, http://www.sigmaaldrich.com/catalog/ProductDetail.do?N4=W272205|ALDRICH&N5=Product%20No.|BRAND_KEY&F=SPEC, 2 pages.*

Ethyl Myristate, Sigma Aldrich, online, http://www.sigmaaldrich.com/catalog/ProductDetail.do?N4=W244503|ALDRICH&N5=Product%20No.|BRAND_KEY&F=SPEC, 2 pages.*

Methyl Palmitate, Sigma aldrich, online, http://www.sigmaaldrich.com/catalog/ProductDetail.do?N4=46235|RIEDEL&N5=Product%20No.|BRAND_KEY&F=SPEC, 1 pages.*

Ethyl palmitate, Sigma Aldrich, online, http://www.sigmaaldrich.com/catalog/ProductDetail.do?N4=W245100|ALDRICH&N5=Product%20No.|BRAND_KEY&F=SPEC, 2 pages.*

Isopropyl Palmitate, Sigma Aldrich, Material Safety Data Sheet. 5 pages. 2009.*

Methyl Myristate, Sigma Aldrich, online, http://www.sigmaaldrich.com, 2 pages: downloaded on: Dec. 18, 2008.*

Ethyl Myristate, Sigma Aldrich, online http://www.sigmaaldrich.com. 2 pages, downloaded on Dec. 18, 2008.*

Methyl Palmitate, Sigma Aldrich, online http://www.sigmaaldrich.com. 2 pages, downloaded on Dec. 18, 2008.*

Ethyl Palmitate, Sigma Aldrich, online http://www.sigmaaldrich.com. 2 pages, downloaded on Dec. 18, 2008.*

Pyatnova et al. "Pheromone Composition for Disorientation of Oriental and Plum Moths", STN Database Accession No. 2002:741452 (2002), European Search Report corresponding to application No. EP 05110016.2-2013, dated Mar. 16, 2006.

European Search Report, corresponding to Application EP04101052, mailed Jul. 28, 2004.

Japanese Official Action corresponding to application No. 2003-071168, dated Jul. 30, 2009.

Japanese Official Action corresponding to application No. 2004-315176, dated Oct. 30, 2009.

* cited by examiner

*Primary Examiner* — Abigail Fisher

(74) *Attorney, Agent, or Firm* — Myers Bigel Sibley & Sajovec, P.A.

(57) ABSTRACT

Provided is a sustained releaser of a sex pheromone having a high release rate, especially preferably of a sex pheromone of an aliphatic acetate compound having 10 to 16 carbon atoms, wherein the release of the sex pheromone is controlled so that it can be released at a constant rate over a control period of a pest insect. More specifically, provided is a sustained pheromone releaser comprising a polymer container and having, enclosed therein, a mixture having a melting point of 15 to 35° C. and being obtained by mixing a sex pheromone substance and a compound having a melting point of 10 to 40° C.

6 Claims, 1 Drawing Sheet

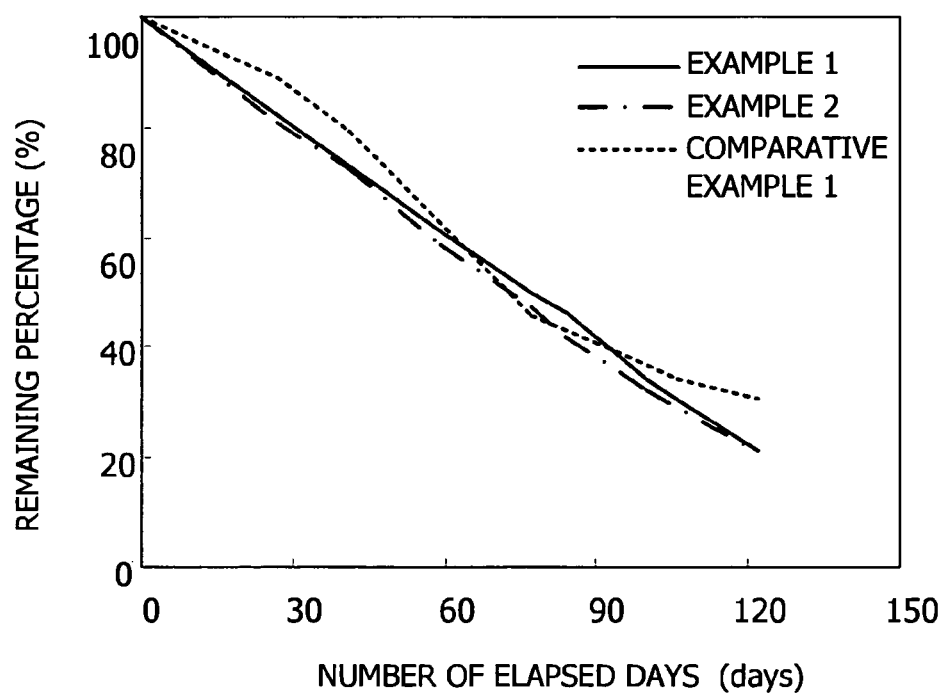

SUSTAINED PHEROMONE RELEASER

RELATED APPLICATIONS

This application claims priority from Japanese Patent Application No. 2004-315176; filed Oct. 29, 2004, the disclosure of which is incorporated by reference herein in its entirety.

BACKGROUND OF THE INVENTION

1. Field of the Invention

The present invention relates to a sustained pheromone releaser to be used in a so-called mating disruption method, that is, a pest insect control method by releasing a sex pheromone substance of the pest insect in a farm, thereby disrupting the mating behavior of the pest.

2. Description of the Related Art

The control of a pest insect by mating disruption is carried out by releasing, in the air, an artificially synthesized sex pheromone of the pest inset to be controlled, suspending it in the air, disrupting the communication between male and female for decreasing a mating rate and thereby controlling the reproduction of the insect pest. A sustained releaser of a sex pheromone is required to be able to release the sex pheromone stably throughout the infestation period of the pest insect. The sustained releaser of a sex pheromone therefore intends to control release of it at a fixed rate for a prolonged period by causing one of the sex pheromone components and a compound such as a geometric isomer thereof to be present together, enclosing it in a plastic container and causing the resulting mixture to permeate through its plastic membrane.

Sex pheromones of pest insects such as Peach Twig Borer (*Anarsia lineatella*), Oriental Fruit Moth (*Grapholita molesta*) and Leaf Roller (*Tortricidae*) are aliphatic acetate compounds having from 10 to 16 carbon atoms. These compounds usually have a low vapor pressure and are released quickly so that a sustained releaser as described above cannot control the release of them over a long period. In order to deal with this problem, various improvements such as thickening of a plastic membrane, using of another kind of plastic or narrowing of a release area are attempted. These attempts have some effects, respectively, but cannot bring about a drastic improvement.

A sustained releaser having, enclosed in a container, a mixture of the above-described sex pheromone and either another sex pheromone or a compound other than the sex pheromone, each having a extremely lower release rate than the above-described sex pheromone, is used (U.S. Pat. No. 5,002,971). This attempts to delay the release of the sex pheromone having a high release rate on basis of decrease of a composition ratio of the sex pheromone because a compound having a much lower release rate is left in the container. However, a release rate of this releaser decreases in the second half compared with that in the first half. Accordingly, during the control period of the pest insect, the sustained releaser has to be placed several times, which inevitably increases the work for it.

SUMMARY OF THE INVENTION

The present invention has been made in order to overcome the above-described problem. An object of the present invention is to provide a sustained releaser of sex pheromone having a high release rate, especially preferably of an aliphatic acetate compound having from 10 to 16 carbon atoms, whereby the release is controlled so that the release rate of the sex pheromone can be kept constant over the control period of a pest insect.

With a view to solving the above-described problem, the present inventors carried out an extensive investigation. As a result, it has been found that a sustained pheromone releaser comprising a polymer container in which a mixture having a melting point of 15 to 35° C. and being obtained by mixing a sex pheromone substance and a compound having a melting point of 10 to 40° C. is enclosed is useful for the resolution of the above-described problem, leading to the completion of the present invention.

The sustained pheromone releaser according to the present invention makes it possible to prevent excessive release of a sex pheromone substance having a low vapor pressure and a high release rate such as aliphatic acetate having from 10 to 16 carbon atoms; and to release the substance at a constant rate even during a low temperature period. In addition, a release rate can be controlled by adjusting the melting point of the mixture while selecting a sex pheromone substance and a non-pheromone substance properly. This makes it possible to release the sex pheromone substance at a constant rate over a period necessary for the control of the pest insect, to save the labor which will otherwise be necessary for placing the releasers several times during the pest insect control period, and to prevent excessive release of the sex pheromone substance.

BRIEF DESCRITPION OF THE DRAWING(S)

FIG. 1 shows a relation between elapsed days after releasers are placed and a remaining percentage of substance(s) enclosed in a container.

DETAILED DESCRIPTION OF THE EMBODIMENTS

The present invention now will be described more fully hereinafter in which embodiments of the invention are provided with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs.

The preferable sex pheromone substance to be used in the present invention may include, but is not particularly limited to, the substances having a low vapor pressure and a high release rate and therefore, having difficulty in continuous release control in a conventional container during the control period of a pest insect. The sex pheromone substance of aliphatic acetate having from 10 to 16 carbon atoms may be most suited. Examples may include decyl acetate, decenyl acetate, decadienyl acetate, undecyl acetate, undecenyl acetate, dodecyl acetate, dodecenyl acetate, dodecadienyl acetate, tridecyl acetate, tridecenyl acetate, tridecadienyl acetate, tetradecyl acetate, tetradecenyl acetate, and tetradecadienyl acetate. The acetate may be used singly or as admixture of two or more.

According to the present invention, by adding a compound having a melting point of 10 to 40° C. to a sex pheromone substance, the melting point of the resulting mixture is adjusted to 15 to 35° C. The preferable compound having a melting point of 10 to 40° C. may be a compound which has compatibility with the sex pheromone substance and is biologically inert to a pest insect, inexpensive, easily available, easy in handling and environmentally friendly. It is preferred that the compound does not penetrate through the polymer material of the container. If the compound has a considerably lower penetration rate than the sex pheromone substance, the compound can be also used. However, the compound which penetrates through the container and stays on the surface of the releaser without evaporation is not preferable because release of the sex pheromone substance is disturbed by the compound staying on the surface.

The compound having a melting point of 10 to 40° C. may be preferably alcohol or ester.

Examples of the alcohol may include decanol, decenol, undecanol, undecenol, dodecanol, dodecenol, dodecadienol, tridecanol, tridecenol, tetradecanol, tetradecenol, tetradecadienol, pentadecanol, pentadecenol, hexadecanol, hexadecenol, hexadecadienol, octadecanol, octadecenol and octadecadienol. Examples of the ester may include sebacate, laurate, palmitate, stearate and arachidate esters. Of these, aliphatic compounds are preferred. They may be linear or side chain, saturated or unsaturated, or monovalent or polyvalent.

In general, the melting point of a mixture is lower than that of a pure substance or solvent because of melting point depression. The compound to be mixed here sometimes has a higher melting point than that of its mixture. It sometimes has a lower melting point than that of its mixture, because when the substance expands by melting, its melting point increases with an increase in pressure. Accordingly, the compound having a melting point of 10 to 40° C. is prefrable.

If the compatibility between a compound having a melting point of 10 to 40° C. and a sex pheromone substance is low, phase separation may occur so that uniform enclosure of them in a container becomes difficult. Even if they can be enclosed in the container, the resulting mixture cannot attain a desired effect. The greater compatibility is therefore preferred.

It may not be preferable that the compound having a melting point of 10 to 40° C. has an influence on the pest insect to be controlled. A sex pheromone substance of another insect pest may be used as the compound having a melting point of 10 to 40° C. insofar as it has no influence on the pest insect to be controlled. However, addition of another sex pheromone substance or an expensive substance may heighten the cost of the releaser so that an inexpensive and easily available substance may be preferred. A substance which needs a special place for handling or has a harmful effect on the environment is not preferred even if it satisfies the above-described conditions.

When the melting point of a mixture obtained by mixing a sex pheromone substance and a compound having a melting point of 10 to 40° C. falls within a range of 15 to 35° C., the release can be controlled properly. The mixture having a melting point lower than 15° C. may decrease the release in a low temperature season such as spring and autumn because the mixture is in the liquid form. The mixture having a melting point exceeding 35° C. may cause excessive release even in a high temperature season such as summer because the mixture is in the solid form.

In general, a solid has a greater volume than a liquid so that the mixture in the solid form has an increased contact area with the inside wall of the container, which leads to an increase in the release amount through the wall. The mixture in the liquid form loses its liquid length as the release proceeds so that the contact area with the inside wall of the container decreases. The mixture in the solid form has a constant release rate especially if one of the components of the mixture has a markedly higher release rate than that of the other component. It is because the component having a lower release rate remains as a solid when the release proceeds so that the contact area with the inside wall of the container does not decrease.

On the other hand, when the mixture is in the liquid form, its contact area with the inside wall of the container is smaller. As the release proceeds, the liquid length decreases, leading to a further reduction in the contact area. Since the mixture is in the liquid form in summer when the temperature is high, it can prevent excessive release while it has brisk release.

The release of a sex pheromone substance having a high release rate is conventionally controlled for example by thickening the wall of a container. However, this method is accompanied with the drawback that a release rate is low in the season when the temperature is low, while excessive release occurs in the season when the temperature is high.

On the other hand, according to the present invention, by changing the form of a mixture to be enclosed in the container in accordance with a temperature change, it is possible to prevent excessive release in a high temperature season while preventing a reduction in a release rate in a low temperature season.

The term "melting point" as used herein means the temperature at which the solid phase of the substance is in equilibrium with the liquid phase under a constant pressure and the melting point is generally equal to the freezing point (Rikagaku Jiten, published by Iwanami Shoten). The melting point here means a value under a pressure of 1 atm.

The content of the sex pheromone substance in the mixture may be preferably 50% by weight or greater but less than 100% by weight. When it is smaller than 50% by weight, a release rate of the sex pheromone substance per releaser decreases so that an increase in the number of releasers per area may be required.

The polymer constituting the container of the present invention may be preferably a polyolefin or an olefin component-containing copolymer. The olefin as used herein may preferably be unsaturated hydrocarbon having one double bond and represented by the formula: $C_nH_{2n}$ wherein n preferably stands for an integer of from 1 to 5. The olefin-component containing copolymer may be a copolymer obtained by using an olefin as one of monomer components. Specific examples may include polyolefin such as polyethylene and polypropylene, and olefin component-containing copolymer (preferably containing at least 90 wt % of olefin component) such as ethylene-vinyl acetate copolymer and ethylene-acrylate copolymer. The sex pheromone substance can penetrate through such a material and release out of the plastic membrane at an appropriate rate. The shape of the container made of polymer may be preferably a tube, a capsule, an ampul or a bag. The container in the tube form may be most suited because it enables constant release of the sex pheromone substance for a prolonged period. When the tube has an inner diameter of from 0.5 to 2.0 mm and thickness of from 0.2 to 1.0 m, release can be maintained at an appropriate rate.

The present invention will hereinafter be described specifically by Examples and Comparative Examples. However, it should not be construed that the present invention is limited to them.

Preparation of a Sustained Pheromone Releaser

A polymer container, more specifically, a polyethylene tube having a predetermined inner diameter and thickness is produced by extrusion. A sex pheromone substance is then mixed with a compound having a melting point of 10 to 40° C. and the mixture is adjusted so as to have a predetermined melting point. The resulting mixture is poured into the polyethylene tube from one end thereof. A pressure is then applied to the both ends of the tube by a heated tongs to melt and seal them. A sustained releaser is obtained by cutting the melted portion. The sustained pheromone releasers thus obtained are placed at equal intervals in a farm which will be subjected to pest insect control. The intervals are based on a release amount of the sex pheromone substance required for the farm.

EXAMPLE 1

A mixed solution having a melting point of 20° C. was prepared by mixing 7 parts by weight of a sex pheromone substance of Peach Twig Borer (PTwb) comprising 85 wt % of E5-decenyl acetate (E5-10: Ac) and 3 parts by weight of n-tetradecanol (n-14: OH). One end of a polymer container (polyethylene tube) having an inner diameter of 1.40 mm and an outer diameter of 2.80 mm was dipped in the mixed solution. Then, the mixed solution was moved into the container by suction. A pressure was applied to the tube by a heated tongs every 200 mm to melt and seal the container. The melted portion was cut to prepare sustained pheromone releasers for the test trial. The amount of the mixed solution enclosed in the container was 240 mg per releaser, of which the amount of PTwB sex pheromone substance was 168 mg.

The releasers prepared in the above manner were placed from April to September on the branches of peach trees which were 1.5 to 2.0 m high from the ground. Five releasers were collected every month and the amount of E5-decenyl acetate remaining in each polymer container was measured. Measurement was carried out by cutting the releasers thus collected into 5 mm pieces, dipping them in acetone for a whole day and night, and analyzing the resulting acetone solution quantitatively by the internal standard method with a gas chromatograph. The amount measured was compared with the amount of a PTwB sex pheromone substance enclosed in the container and a remaining percentage was calculated. The results are shown in FIG. 1.

EXAMPLE 2

Sustained pheromone releasers were prepared for the test trial by enclosing, in each polymer container similar to that employed in Example 1, 240 mg of the mixed solution having a melting point of 20° C. and being obtained by mixing 7 parts by weight of PTWB sex pheromone comprising 85 wt % of E5-decenyl acetate (E5-10: Ac) and 3 parts by weight of butyl stearate. The resulting releasers were placed on the same day in the same farm as in Example 1, and collected on the same day as in Example 1. A remaining percentage was calculated in the same manner as in Example 1. The results are shown in FIG. 1.

COMPARATIVE EXAMPLE 1

Sustained pheromone releasers were prepared for the test trial by enclosing, in each polymer container similar to that employed in Example 1, 240 mg of a Peach Wig Borer (PTwb) sex pheromone substance alone comprising 85 wt % of E5-decenyl acetate (E5-10: Ac) . The resulting releasers were placed on the same day in the same farm as in Example 1, and collected on the same day as in Example 1. A remaining percentage was calculated in the same manner as in Example 1. The results are shown in FIG. 1.

It is evident from FIG. 1 that the releasers obtained in Example 1 show a constant release rate of the sex pheromone substance irrespective of the number of elapsed days, in other words, irrespective of variations in temperature, while the releasers obtained in Comparative Example 1 show changes in the release of the sex pheromone substance depending on the number of elapsed days.

The invention claimed is:

1. A sustained pheromone releaser comprising a polymer container having, enclosed therein, a mixture having a melting point of 15 to 35° C., wherein said mixture comprises:
   a sex pheromone substance that is an aliphatic acetate having 10 to 16 carbon atoms; and
   a compound that has a melting point of 10 to 40° C., has compatibility with the sex pheromone substance, is biologically inert to a pest insect to be controlled and is an ester selected from a group consisting of sebacate, laurate, palmitate, stearate and arachidate esters,
   wherein said polymer container is in the form of a tube, an ampul or a bag made of a polyolefin or an olefin component-containing copolymer, and wherein the amount of the sex pheromone substance in the mixture is 70% or greater and less than 100%.

2. The sustained pheromone releaser according to claim 1, wherein said mixture consists of:
   a sex pheromone substance that is an aliphatic acetate having 10 to 16 carbon atoms; and
   a compound having a melting point of 10 to 40° C. that is an ester selected from the group consisting of sebacate, laurate, palmitate, stearate and arachidate esters.

3. A sustained pheromone releaser comprising a polymer container having, enclosed therein, a mixture having a melting point of 15 to 35° C., wherein said mixture comprises:
   a sex pheromone substance that is an aliphatic acetate having 10 to 16 carbon atoms; and
   a compound that has a melting point of 10 to 40° C., has compatibility with the sex pheromone substance, is biologically inert to a pest insect to be controlled and is an alcohol selected from the group consisting of undecanol, dodecanol, tridecanol, tridecenol, tetradecanol, tetradecenol, tetradecadienol, pentadecanol, pentadecenol, hexadecanol, hexadecenol, hexadecadienol, octadecenol and octadecadienol,
   wherein the amount of the sex pheromone substance in the muixture is 70% or greater and less than 100%.

4. The sustained pheromone releaser according to claim 3, wherein said polymer container is in the form of a tube, an ampul or a bag made of a polyolefin or an olefin component-containing copolymer.

5. The sustained pheromone releaser according to claim 3, wherein said mixture consists of:
   a sex pheromone substance that is an aliphatic acetate having 10 to 16 carbon atoms; and
   a compound having a melting point of 10 to 40° C. that is an alcohol selected from the group consisting of undecanol, dodecanol, tridecanol, tridecenol, tetradecanol, tetradecenol, tetradecadienol, pentadecanol, pentadecenol, hexadecanol, hexadecenol, hexadecadienol, octadecenol and octadecadienol.

6. The sustained pheromone releaser according to claim 5, wherein said polymer container is in the form of a tube, an ampul or a bag made of a polyolefin or an olefin component-containing copolymer.

* * * * *